Nov. 28, 1950 M. HAGERSTROM Plant Pat. 993
STRAWBERRY PLANT
Filed Nov. 19, 1949
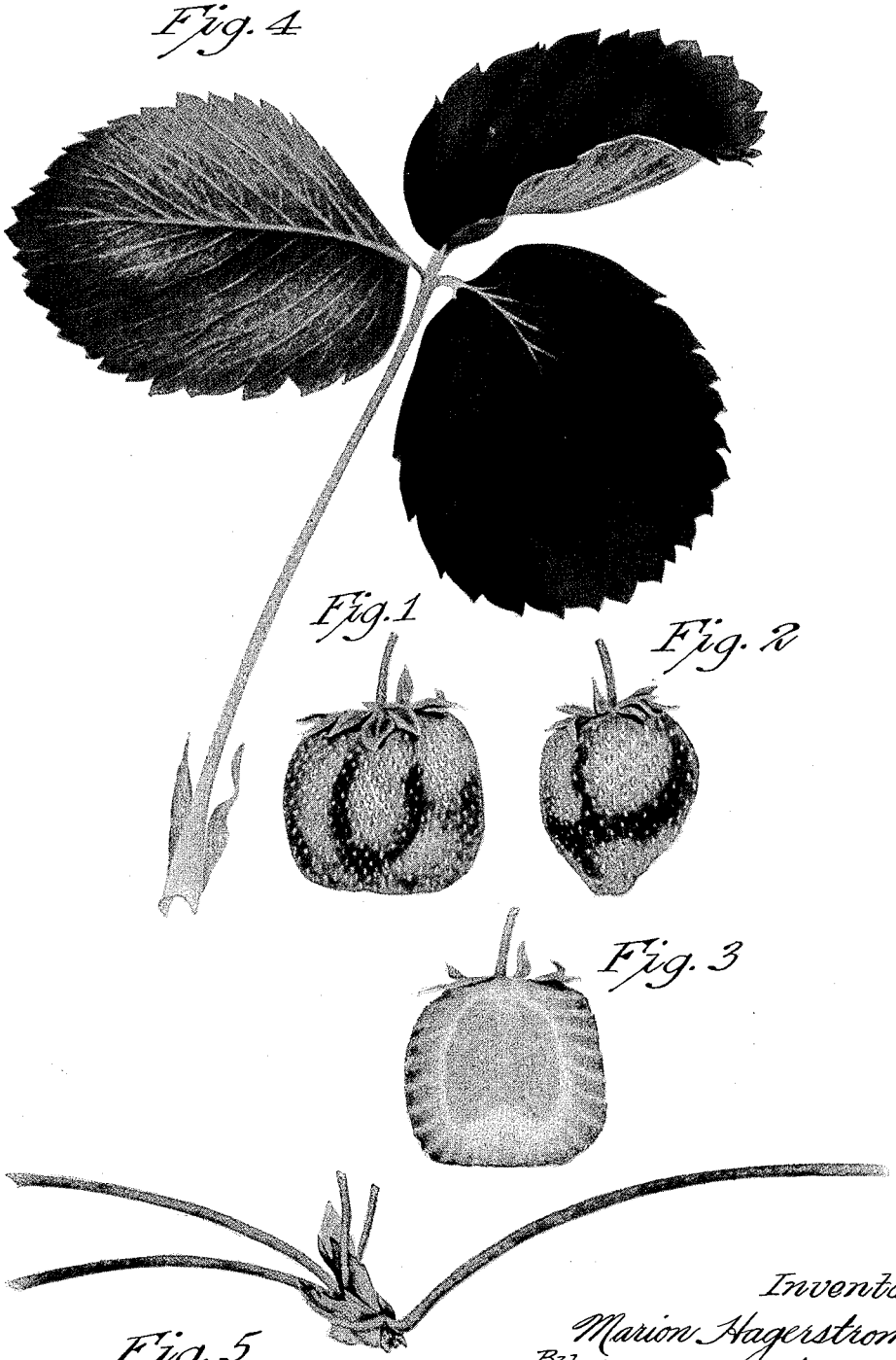
Inventor
Marion Hagerstrom
By Williamson & Williamson
Attorneys Patented Nov. 28, 1950

Plant Pat. 993

UNITED STATES PATENT OFFICE

993

STRAWBERRY PLANT

Marion Hagerstrom, Enfield, Minn., assignor of one-half to Carl R. Hagerstrom, Enfield, Minn.

Application November 19, 1949, Serial No. 128,344

1 Claim. (Cl. 47—62)

My invention relates to a new and distinct variety of strawberry plant, which is the result of a cross between the Wayzata, an everbearing plant, and the Fairfax, a June bearing plant.

The mother plant was developed and produced on my farm at Enfield, Minnesota, and I have asexually reproduced a large number of plants from the original mother plant by transplanting rooted runner plants on my said farm.

The object of the cross was to produce a new strawberry plant embodying certain of the desirable characteristics of its parents and certain characteristics which are greatly improved over either of the parents.

My new variety embodies the hardy reproductivity of the Fairfax, and produces a mildly acid sweet tangy berry, sweeter than the Wayzata and substantially similar to the Fairfax, which has a rich dark red color, darker than the Wayzata but slightly lighter than the Fairfax.

In the accompanying drawings is illustrated a berry, leaf, and runner plant of typical size and shape. In said drawings, Fig. 1 is a front elevation of a typical berry.

Fig. 2 is a side elevation of the berry shown in Fig. 1.

Fig. 3 is a central vertical longitudinal section through the berry shown in Figs. 1 and 2.

Fig. 4 is an elevational view showing the stem with typical leaves thereon, and

Fig. 5 is an elevational view of a typical runner showing the first runner plant which usually sprouts at least two stems.

I now refer more in detail to my new variety of strawberry and to the plant bearing said berry, the plant and berry have the following distinctive characteristics which combine to distinguish them from the other known varieties:

The plant is extremely prolific and produces a large number of very hardy runners. An average number of rooted runner plants for each mother plant has been fifteen as of September 5, 1949, and many mother plants produced more than fifteen rooted runner plants. The plants are very hardy, with good disease and insect resistance. The plant is extremely frost resistant, being hardier than either the Fairfax or the Wayzata, and has relatively long roots to produce far above average drought resistance, as well as average resistance to wet weather, which is equal to the Fairfax and Wayzata.

The berry has a rich, mildly acid, sweet, tangy flavor and the flesh of the berry is relatively firm and of very good durability. The berry as illustrated in the drawings is larger than the Wayzata, but slightly smaller than the Fairfax, is conical wedge-shaped and some berries are specifically wedge-shaped. The surface of the berry is somewhat irregular. The color of the berry is a rich dark red throughout and has a relatively small core. The surface is lustrous with bright seeds. The berry is particularly characterized by its fine keeping quality and delicious sweet tangy taste.

My everbearing strawberry plant starts blooming about May 5 for the June crop and continues to bloom for the June crop until about June 18. The first berries for the June crop appear about June 6 and the date of the last bearing for the June crop is about July 1. The first blossoms for the fall crop appear about June 18 and the fall crop beings bearing about July 6 and continues to bear until the first killing frost.

The plant is particularly characterized by its extreme hardiness and prolific production of hardy runner plants which bear a heavy crop of fruit as a rule until the first frost, as well as its adaptability to growing very successfully in all types of soil.

As a convenient summary, the following is a detailed description of this new variety of strawberry plant:

*Plant characteristics*

*Size.*—Medium to large roots, thick and unusually long root system (longer, heavier and more vigorous than either parent.)

*Crown size.*—About $\frac{7}{16}$ of an inch thick, about 1 inch in length, (similar to the 2 parents).

*Leaves.*—Similar leaf structure to the 2 parents, generally trifoliate but not uncommon to have 4 or 5 leaflets on a single petiole.

*Petiole.*—Somewhat longer and heavier than the 2 parents.

*Leaflets.*—Generally rounded periphery with uniform serrations. Said leaflets are approximately as broad as they are long and are generally cupped upwardly similar to the Fairfax. Upper surface of the leaf is smooth and the lower surface has medium pubescence and is convex in shape. The upper surface is a relatively dark green while the lower surface is light green in color.

*Runners.*—Very hardy, very freely produced, the first plant from the mother plant usually producing two upright stems. By September 5 the mother plants have produced an average of 15 rooted runner plants each.

*Flower stems.*—Thick and generally upright, partially exposed.

*Flower.*—Blossoms are large and perfect, resembling the parents and nearly all produce a salable fruit. They are self-pollinizing.

*Sex.*—Bisexual.

*Fruit stems.*—Heavy and upright with many branch stems.

*Soil.*—Plants have been grown very successfully in a large variety of soil types.

*Culture.*—Moderate to frequent.

*Disease resistance.*—Good; about the same as Fairfax and Wayzata.

*Insect resistance.*—Good; about the same as Fairfax and Wayzata.

*Frost resistance.*—Above average; hardier than both parents.

*Rain resistance.*—Similar to Fairfax and Wayzata.

*Drouth resistance.*—Superior to either Fairfax or Wayzata.

*Fruit.*—Condition when described—prime.

*Date described.*—July 28.

*Size.*—Large; larger than Wayzata, but slightly smaller than Fairfax.

*Surface contour.*—Irregular.

*Shape.*—Generally wedge-shaped in early fruiting season; more broadly wedge-shaped and later becomes more conical in shape.

*Fruit stems.*—Very slight pubescence and about equal length to the parents.

*Aspect.*—Glossy lustre with uniform, dark red color substantially throughout the entire berry, including the center.

*Seeds.*—Conspicuous and bright, and are flush with the berry's surface.

*Core.*—Very small at the extreme top of the berry and reddish in color.

*Calyx.*—Flat against the upper berry surface; surface is light green and generally smooth; very scant pubescence.

*Flesh.*—Juicy and firm, firmer than Wayzata and generally similar to Fairfax.

*Flavor.*—Mildly acid with a sweet, rich, tart flavor.

*Fruit*

*Quality.*—Very high, good for shipping.

*Uses.*—Extremely good for canning and freezing, as well as good dessert quality.

The strawberry described above and the plant producing the same may vary in slight details, depending upon the weather conditions and the soil conditions under which they are grown.

What I claim is:

An everbearing strawberry plant substantially as herein shown and described characterized by the large number of hardy fruit producing runner plants, and by a firm generally conical-wedge shaped berry, dark red in color, with a lustrous irregular surface and a rich, mildly acid, sweet, tangy flavor, and particularly adapted to grow successfully and prolifically in a large number of soil types under a variety of extreme weather conditions.

MARION HAGERSTROM.

No references cited.